United States Patent [19]
Harrison et al.

[11] Patent Number: 5,108,375
[45] Date of Patent: Apr. 28, 1992

[54] CLOSED SYSTEM CANULATING DEVICE

[76] Inventors: Samuel W. Harrison, 4003 Scenic Dr., Shreveport, La. 71119; Catrell McCulloch, 3852 Murvon St., Shreveport, La. 71109; Lawrence E. Mosley, 135 E. 79th St., Shreveport, La. 71106

[21] Appl. No.: 762,628

[22] Filed: Sep. 19, 1991

[51] Int. Cl.⁵ ............................................. A61M 5/00
[52] U.S. Cl. ................................... 604/167; 604/168; 604/171
[58] Field of Search ............... 604/164, 167, 168, 280, 604/169, 171

[56] References Cited

U.S. PATENT DOCUMENTS

| | | | |
|---|---|---|---|
| 3,352,306 | 11/1967 | Hirsch | 604/168 |
| 3,825,001 | 7/1974 | Bennet et al. | 604/171 |
| 4,046,144 | 9/1977 | McFarlane | 604/168 |
| 4,073,297 | 2/1978 | Kopp | 604/164 |
| 4,327,723 | 5/1982 | Frankhouser | 604/171 |
| 4,365,630 | 12/1982 | McFarlane | |
| 4,652,256 | 3/1987 | Vaillancourt | 604/52 |
| 4,819,659 | 4/1989 | Sitar | 128/764 |
| 4,828,548 | 5/1989 | Walter | 604/164 |
| 4,840,613 | 6/1989 | Balbierz | 604/171 |
| 4,944,728 | 7/1990 | Carrell et al. | 604/164 |
| 4,955,871 | 9/1990 | Thomas | 604/217 |
| 4,960,412 | 10/1990 | Fink | 604/167 |
| 5,013,304 | 5/1991 | Russell et al. | 604/167 |
| 5,030,207 | 7/1991 | Mersch et al. | 604/168 |
| 5,053,013 | 10/1991 | Ensmuger et al. | 604/167 |
| 5,053,014 | 10/1991 | Van Heugsten | 604/167 |

OTHER PUBLICATIONS

Arrow Percutanrous Sheath Introducer Product, Jobes et al., May 1990.

*Primary Examiner*—Paul J. Hirsch
*Attorney, Agent, or Firm*—John M. Harrison

[57] ABSTRACT

A closed system canulating device for arterial and venous catherization, which includes a reservoir attached to the hub of a needle assembly and provided with an internal wire guide and valve to facilitate canulating an artery or vein with the needle and containing blood flashback in the reservoir during the canulation procedure. After canulation of the artery or vein is accomplished, a catheter guide wire is inserted through the valve and the wire guide located in the reservoir, into the needle hub and needle and finally into the artery or vein, to facilitate completion of the catherization procedure.

20 Claims, 2 Drawing Sheets

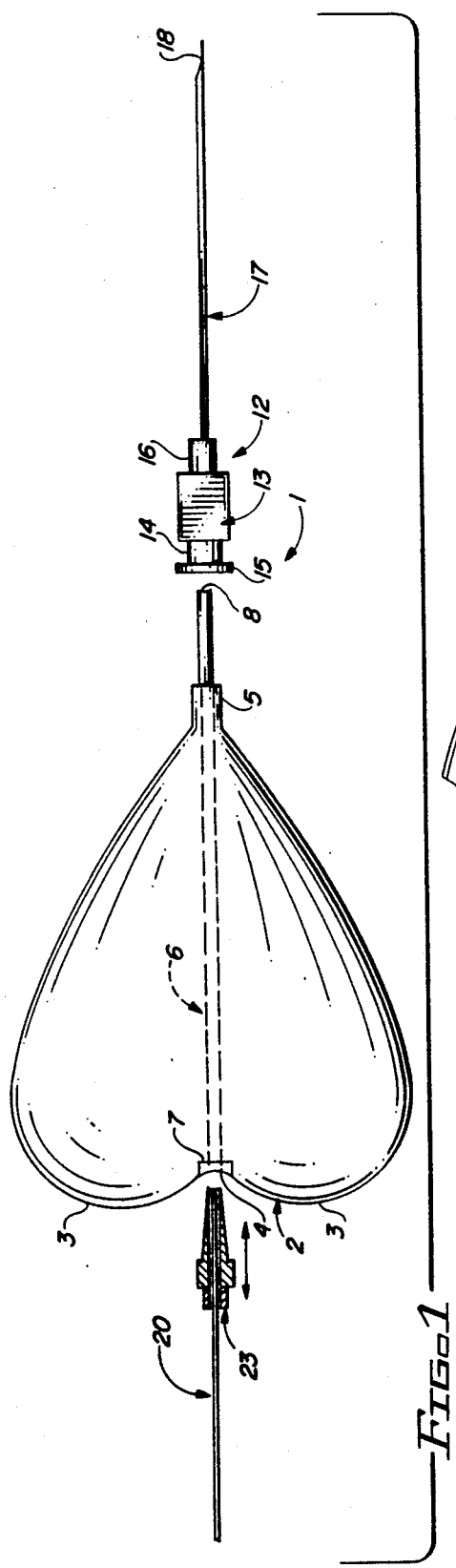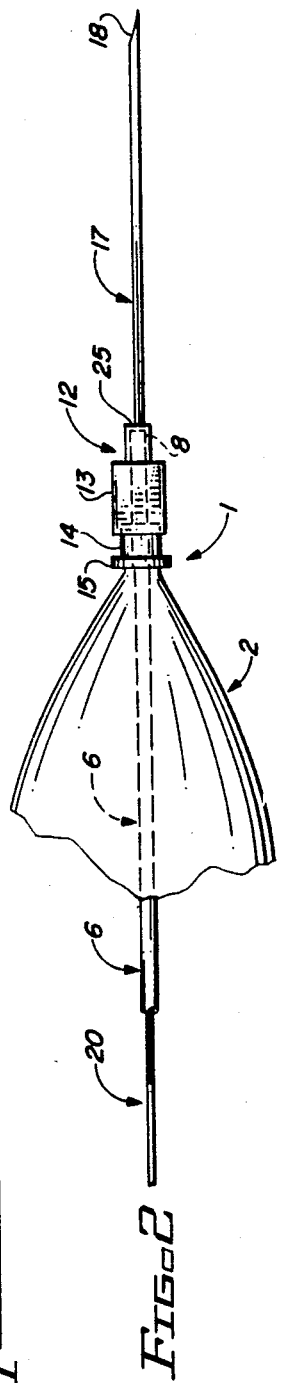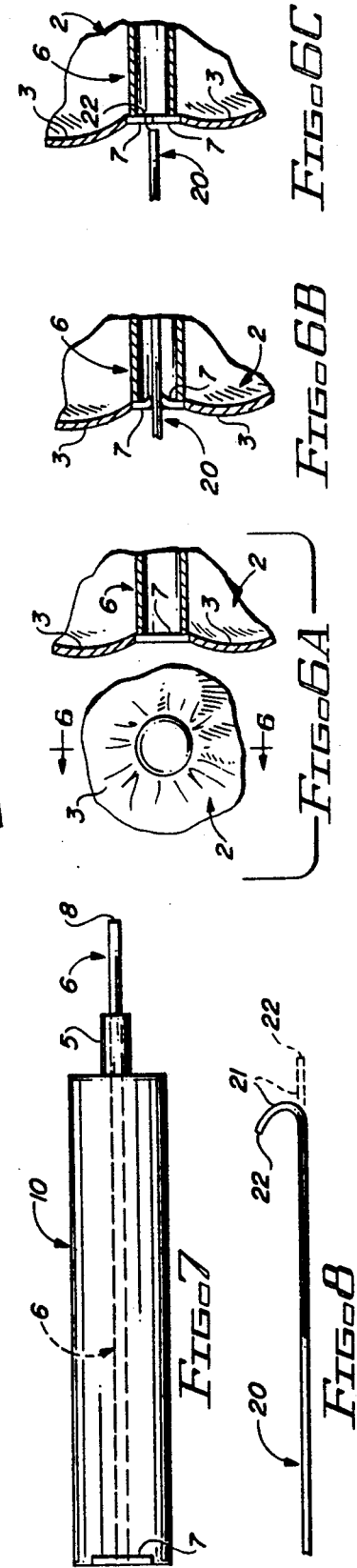

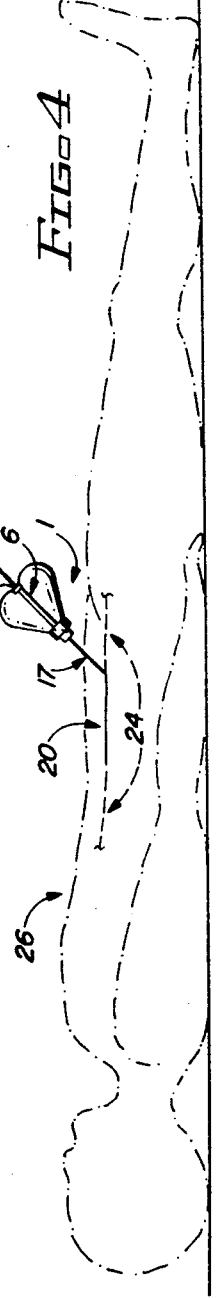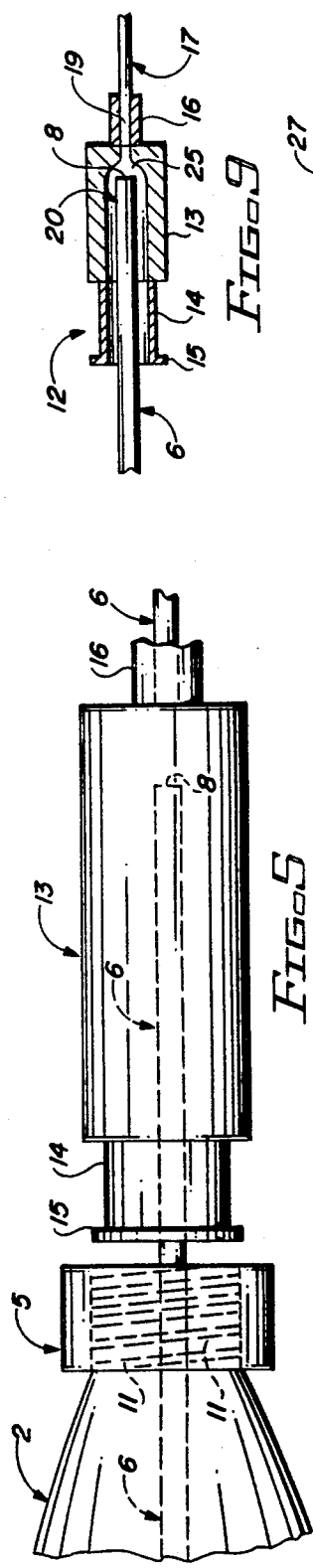

CLOSED SYSTEM CANULATING DEVICE

BACKGROUND OF THE INVENTION

1. Field of the Invention

This invention relates to heart catherization and more particularly, to a closed system canulating device for canulating blood vessels, including arteries and veins and preventing uncontrolled blood flashback from the canulated needle. In a preferred embodiment the closed system canulating device includes a needle assembly, a reservoir having a tip attached to the hub of the needle assembly for containing 5-10 cc. of flashback blood, a wire guide provided in the interior of the reservoir and extending beyond the reservoir tip into the needle hub and a valve seated in the opposite end of the wire guide. The hub of the needle assembly may be shaped integrally with, or attached to the reservoir tip and the needle assembly and reservoir may be used to canulated an artery or vein and contain blood flashback in the reservoir. The reservoir remains in place on the needle assembly after canulation while the needle is in the vessel lumen, to contain pulsatile blood flashback and a catheter guide wire is inserted through the valve and wire guide, into the needle hub and through the needle into the artery or vein, to facilitate completion of the catherization procedure.

Catherization procedures, including left and right heart catherization, involve achieving vascular access by needle puncture. Once the needle has been canulated and positioned within the vessel lumen, a flexible guide wire can be advanced through the needle and well into the central vasculature. When this needle is withdrawn, the guide wire remains in the intravascular position and provides a means of introducing the desired catheter or catheters. Unfortunately, when the canulating needle is inserted into an artery, pulsatile blood flow is realized under relatively high pressure from the needle hub. This uncontrolled spurting of blood may strike the attending physician, as well as anyone else in the area.

Venous catherization can be performed through the femoral, internal jugular, subclavian or median antecubital vein, whereas arterial catherization can be accomplished through the femoral, brachial or axillary artery. At termination of the catherization procedure, the catheters and introducing sheaths are withdrawn and bleeding from the puncture sites is typically controlled by application of direct pressure.

The femoral artery and adjacent vein are the most commonly used vessels for percutaneous diagnostic cardiac catherization. The femoral artery typically lies at the midpoint of the inguinal ligament and can be palpated over a several centimeter span distal to the ligament. The femoral vein lies approximately one finger breadth medial to the artery, along a parallel course. Once the inguinal ligament and femoral artery have been identified, the femoral artery is palpated along its course using the three middle fingers of a left hand. With the lift hand remaining in place, transverse skin punctures are made over the femoral artery and vein using the tip of a scapel blade. The femoral artery is then punctured by inserting a needle through the lateral skin nick at about a 45 degree angle along the axis of the femoral artery, as palpated by the three middle fingers of the left hand. When the tip of the needle enters the lumen of the femoral artery, blood flashback is normally experienced responsive to pulsatile arterial blood flow. Since this blood typically spurts from the hub of the needle with considerable force and may strike the physician or assistant or both, who are standing beside the supine patient, the risk of spreading blood-bourne pathogens such as HIV virus (AIDS), hepatitis or syphilis, in non-exclusive particular, is present. The closed system canulating device of this invention is designed to collect and contain blood flashback as the tip of the needle enters the lumen of a vessel such as the femoral artery and during the catheter guide wire insertion procedure.

2. Description of the Prior Art

Various techniques have been used to produce or eliminate the flashback of blood from blood vessels such as arteries and veins during catherization procedures. U.S. Pat. No. 4,365,630, dated Dec. 28, 1982, to Richard H. McFarlane, discloses a "Flashback Chamber for Catheter". The patent details a plastic catheter having an improved flashback chamber to insure sequential filling with blood for visual observation of blood flow. A "Closed System Catheter With Guide Wire" is detailed in U.S. Pat. No. 4,652,256, dated Mar. 24, 1987, to Vincent L. Vaillancourt. The catheter system is designed for introduction and placement of a flexible catheter into the lumen of an artery or vein. A guide wire is provided for insertion through a hollow needle and the needle hub is provided with a skirt and extends through the hub and into flow communication with a flashback chamber. The guide wire is manipulated forwardly by grasping the wire and feeding the wire through the flashback chamber into the lumen after needle penetration has been made, as indicated by the blood flashback. U.S. Pat. No. 4,819,659, dated Apr. 11, 1989, to Dennis L. Sitar, details a "Blood Withdrawal Device With Movable Needle Guard Member". The unitary structure includes a tube-holding section and a locking section for locking a guard member in a permanently forward position, which covers the tip of the needle. A "Safety Catheter" is detailed in U.S. Pat. No. 4,828,548, dated May 9, 1989, to Gregary W. Walter. The safety catheter includes disposal apparatus for the safe disposal of a medicinal needle after use. The apparatus utilizes a container with a vacuum and a piston attached to one side of the needle which protrudes, ready for use. After use of the needle, one side of the piston is exposed to ambient pressure and the needle is retracted into the container for safe disposal. An "Intravenous Catheter Placement Device" is detailed in U.S. Pat. No. 4,944,728, dated Jul. 31, 1990, to Michael W. Carrell, et al. The intravenous catheter placement device includes a tubular catheter section concentrically surrounding an elongated tubular needle which has a bias cut point projecting from one end of the catheter section and used to lead the catheter section into a blood vessel. A protective sheath sub-assembly is connected to the needle and to the catheter section to facilitate withdrawal of the needle through the tubular catheter section into a protective, rigid tubular sheath, leaving the catheter section in place in the blood vessel. Locking elements on the protective tubular sheath sub-assembly lock the needle in the protective position. A "Single-Use Disposable Syringe" is detailed in U.S. Pat. No. 4,955,871, to Ronny D. Thomas. The syringe includes a reservoir formed of two sheets of thermoplastic material having expanded central portions that form a pair of convex domes, both of which are compressible, and a connecting member which spaces the domes. In response to complete compression of both of the central portions together, the reservoir substantially collapses and each of the domes becomes concave, to prevent the reservoir from being reformed and undesirable re-use of the syringe. After partial compression of both the central portions together and partial collapse of the reservoir, the central portions expand to reform the reservoir and draw fluid into the reservoir, therby aspirating a hypodermic needle. U.S. Pat. No. 5,030,207, dated Jul. 9, 1991, to Stephen H. Mersch, et al, details an "Instaneous Vein Entry Indicator for Intravenous Needle". The device indicates when an intravenous needle has entered a vein, by use of a solid fiber optic mounted in the needle for showing visual instaneous vein entry. The distal end of the fiber optic is polished for flush positioning with the distal point of the needle and the fiber optic is sized to include an outer diameter which will extend through the cannula of the needle. This polished distal end reflects color, such as red blood, immediately upon vein entry and exposure of blood to the magnifying system forming a part of the invention at the rear, or proximal end of the fiber optic. The user observes immediate vein entry without any blood flow or exposure to blood.

It is an object of this invention to provide a closed system canulating device for canulating a blood vessel and containing flashback of blood from the vessel upon entry of the needle into the vessel.

Another object of this invention is to provide a closed system canulating device for canulating an artery or vein and facilitating insertion of a catheter guide wire through the canulating needle without spreading pulsatile blood from the artery or vein.

A still further object of this invention is to provide a closed system canulating device for canulating an artery or vein and preventing uncontrolled spurting of blood from pulsatile blood flow, which canulating device includes a flashback blood receptacle attached to a canulating needle and fitted with a wire guide and valve for receiving a catheter guide wire and containing flashback pulsatile blood flow after the needle has entered the lumen of the artery or vein.

Yet another object of the invention is to provide a closed system canulating device which includes a canulating needle having a hub connected to or shaped integrally with a reservoir for containing flashback blood, a hollow wire guide extending longitudinally through the reservoir and terminating in the needle hub and a self-sealing, resilient hemostatic valve located in the wire guide for sealing a catheter guide wire in the wire guide as the catheter guide wire is inserted in the wire guide, needle and into the lumen of a canulated blood vessel. The wire guide may be spaced from the needle canula or lumen inside the needle hub or seated against the needle lumen and fitted with one or more slots or openings to facilitate flashback blood flow from the blood vessel through the needle lumen and into the reservoir.

SUMMARY OF THE INVENTION

These and other objects of the invention are provided in a new and improved closed system canulating device which includes a reservoir of selected shape and size and having an internal hollow wire guide, a one-way hemostatic valve located in the wire guide and a tip for engaging a canulating needle, such that insertion of the needle in the lumen of an artery or vein causes a pulsatile blood flow which flashes back through the needle, to be collected and contained in the reservoir. A catheter guide wire can be inserted through the valve, wire guide and needle, into the lumen of the artery or vein to facilitate later removal of the needle and insertion of various catheters and sheaths, as deemed necessary. The guide wire can be removed and additional guide wires reinserted into the artery or vein through the closed system canulating device without loss of additional blood, due to self-sealing closure of the hemostatic valve with each wire removal.

BRIEF DESCRIPTION OF THE DRAWING

The invention will be better understood by reference to the accompanying drawing, wherein:

FIG. 1 is a side view of a preferred embodiment of the closed system canulating device of this invention in disassembled configuration;

FIG. 2 is a perspective view of the closed system canulating device in assembled configuration;

FIG. 3 is a perspective view of the closed system canulating device in blood vessel-canulating configuration after insertion of a canulating needle into the femoral artery of a patient;

FIG. 4 is a perspective view of the closed system canulating device in canulating configuration, with the canulating needle inserted in the femoral artery and a catheter guide wire extending through the canulating device, including the canulating needle, into the femoral artery;

FIG. 5 is an enlarged side view of a conventional "luer-lock" needle-hub locking mechanism for removably attaching a needle assembly to a flashback blood reservoir in the closed system canulating device of this invention;

FIG. 6 is an enlarged end view of the closed system canulating device, more particularly illustrating a preferred resilient hemostatic valve element;

FIG. 6A is a sectional view taken along line 6—6 of the hemostatic valve illustrated in FIG. 6;

FIG. 6B is a sectional view taken along line 6—6 of the hemostatic valve illustrated in FIG. 6, with a catheter guide view extending therethrough;

FIG. 6C is a sectional view taken along 6—6 of the hemostatic valve illustrated in FIG. 6, with the catheter guide wire removed;

FIG. 7 is a side view of a second preferred embodiment of the closed system canulating device of this invention;

FIG. 8 is a side view of a conventional catheter guide wire fitted with a curved, flexible guide wire end.

FIG. 9 is a sectional view of a first preferred critical clearance wire guide design to facilitate entry of flashback blood into the reservoir;

FIG. 10 is a sectional view of a second preferred slotted wire guide design;

FIG. 11 is a side view, partially in section, of a third preferred apertured wire guide design.

DESCRIPTION OF THE PREFERRED EMBODIMENTS

Referring initially to FIGS. 1 and 2 of the drawings, the closed system canulating device of this invention is generally illustrated by reference numeral 1. In a first preferred embodiment the canulating device 1 is characterized by a heart-shaped reservoir 2, defined by a pair of reservoir lobes 3, which meet at a lobe intersection 4 and extend to define a reservoir tip 5, as illustrated. A hollow wire guide 6 is located longitudinally inside the heart-shaped reservoir 2, extends from the lobe intersection 4 through the reservoir tip 5 and terminates at a wire guide tip 8, extended from the reservoir tip 5, as illustrated in FIG. 1. A resilient, one-way hemostatic valve 7 is secured inside the wire guide 6 at the lobe intersection 4, for purposes which will be hereinafter further described.

Referring now to FIGS. 1, 2, 5 and 9 of the drawings, it will be appreciated by those skilled in the art that the heart-shaped reservoir 2 can be connected to the hub 13 of a needle assembly 12 by means of a "slip fit", as illustrated in FIGS. 1 and 2 or by operation of a conventional locking mechanism such as the "luer lock", having threads 11, provided in the reservoir tip 5, which threadably receive a cooperating hub flange 15, extending from the hub neck 14 of the hub 13 in the needle assembly 12, as illustrated in FIG. 5. Alternatively, it will be further appreciated by those skilled in the art that the heart-shaped reservoir 2 can be permanently connected to the hub 13 of the needle assembly 12, as desired. Whether the needle assembly 12 is connected to the reservoir tip 5 of the heart-shaped reservoir 2 in permanent or removable fashion, an important embodiment of the invention is the positioning of the wire guide tip 8 in close proximity to, but spaced from, the needle lumen 19 at the base of the needle mount 16 of the hub 13, as illustrated in FIG. 9. The hollow needle 17 is seated in a cylindrical needle mount 16 and the opposite end of the needle 17 terminates in a needle bevel 18, in conventional fashion. It will be appreciated that a critical clearance 25 must be maintained between the wire guide tip 8 of the wire guide 6 and the corresponding needle lumen 19. This critical clearance 25 is necessary to facilitate the flow of pulsatile blood which may flash back from the artery or vein penetrated by the needle bevel 18 of the needle 17 when the needle 17 is canulated in the artery or vein. However, the critical clearance 25 must be sufficiently small to maintain elongation of the flexible, normally curved guide wire end 21 of a catheter guide wire 20, to prevent the guide wire tip 22 from prematurely curling into the characteristic "J" configuration illustrated in FIG. 8, as the guide wire tip 22 traverses the critical clearance 25 and moves into the bore of the needle mount 16, also as illustrated in FIG. 9. This objective is aided by the conventional internal hub bevel 13a provided in the end of the hub 13 at the needle mount 16. Accordingly, a catheter guide wire 20 may be inserted through the resilient and easily penetrated one-way hemostatic valve 7 at the lobe intersection 4 of the heart-shaped reservoir 2, using a conventional stylette 23. The catheter guide wire 20 is then pushed through the wire guide 6, across the critical clearance 25 and through the bore in the needle mount 16 and the needle lumen 19, into the femoral artery 24, as hereinafter further described, after the needle 17 is canulated in the femoral artery 24.

Referring to FIGS. 10 and 11, blood flashback from the femoral artery 24 into the heart-shaped reservoir 2 may also be effected in the canulating device 1 by providing one or more slots 27 (FIG. 10) or holes 28 (FIG. 11) under circumstances where the needle assembly 2 is attached to the heart-shaped reservoir 2 such that the wire guide tip 8 is extended into or is positioned very close to the needle lumen 19 at the needle mount 16. This design facilitates flashback blood flow from the needle lumen 19 into the wire guide 6 and through the slots 27 or holes 28, into the heart-shaped reservoir 2.

Referring now to FIGS. 3, 4 and 9-11 of the drawings, the canulating device 1 utilized in the heart-shaped reservoir 2 is used to canulate the femoral artery 24 in a patient 26 by initially palpating the femoral artery 24 as described above, until the operator feels the transmitted pulsation of the femoral artery 24. The canulating device 1 is then poised above the patient, with the needle bevel 18 pointed upward and is subsequently inserted into the lumen of the femoral artery 24, typically using a single-wall puncture technique. The pulsatile blood flow then causes a flashback of blood through the hollow needle 17 and the bore of the needle mount 16, and through the critical clearance 25 or the slot(s) 27 or holes 28, depending upon the selected guide wire 6 design, into the heart-shaped reservoir 2. With the needle 17 securely positioned in the lumen of the femoral artery 24, the stylette 23 and guide wire tip 22 in the guide wire end 21 of a catheter guide wire 20 are inserted through the resilient one-way hemostatic valve 7 at the lobe intersection 4 of the heart-shaped reservoir 2 and the catheter guide wire 20 is then extended through the wire guide 6. Further extension of the catheter guide wire 20 through the wire guide 6 causes the guide wire tip 22 to traverse the critical clearance 25 or more directly into the needle lumen 19 in elongated configuration, before the guide wire end 21 can curve into the "J" configuration illustrated in FIG. 8. The elongated guide wire tip 22 therefore continues to traverse the needle lumen 19 of the needle 17 and finally moves into the lumen of the femoral artery 24, where the guide wire end 21 again assumes by "memory" the "J" shaped configuration illustrated in FIG. 8. The catheter guide wire 20 can then be manipulated into the heart or other organ as desired, in conventional fashion.

Referring now to FIG. 7 of the drawings, it will be appreciated by those skilled in the art that an elongated reservoir 10 may be used in place of the heart-shaped reservoir 2 for receiving flashback blood during the canulating procedure described above. It will be further appreciated by those skilled in the art that reservoirs of any desired configuration and volume may be utilized in the closed system canulating device of this invention, it being only necessary to provide an internal wire guide 6 of desired design and an associated one-way hemostatic valve 7 to facilitate insertion of one or more catheter guide wires 20 in sequence and prevent splattering of blood resulting from the pulsatile blood flow through the canulated artery or vein.

It will also be appreciated by those skilled in the art that the catheter guide wire 20 may be removed from the canulating device 1 and another or additional catheter guide wires 20 reinserted through the one-way hemostatic valve 7, which automatically seals when each catheter guide wire 20 is withdrawn. Accordingly, the one-way hemostatic valve 7 serves to automatically close upon withdrawal of a catheter guide wire 20 and yet facilitates insertion of additional catheter guide wires 20, in sequence, using the respective stylettes 23, to further contain pulsatile blood flow in the corresponding reservoir during the catherization procedure. The hemostatic valve 7 may be constructed of a resilient, self-sealing material such as a rubber or plastic wafer, membrane or disc, in non-exclusive particular, of sufficient thickness to facilitate penetration by the stylette 23 which houses the guide wire tip 22 of the catheter guide wire 20.

It is understood by those skilled in the art that either the heart-shaped reservoir 2 or the elongated reservoir 10, as well as a reservoir of any other desired configuration may be shaped from plastic, rubber or other materials well known to those skilled in the art and the reservoir may be movably or permanently fitted to a conventional needle assembly 12 or a specially designed needle assembly, as desired.

Accordingly, while the preferred embodiments of the invention have been described above, it will be recognized and understood that various modifications may be made in the invention and the appended claims are intended to cover all such modifications which may fall within the spirit and scope of the invention.

Having described my invention with the particularity set forth above, what is claimed is:

1. A closed system canulating device for receiving a catheter guide wire, comprising needle means adapted for canulating a blood vessel; reservoir means carried by said needle means for containing flashback blood from the blood vessel when the blood vessel is canulated by said needle means; a hollow wire guide extending through said reservoir for receiving the catheter guide wire and guiding the catheter guide wire through said needle means and into the blood vessel; and valve means provided in said wire guide for sealing the catheter guide wire in said wire guide and substantially preventing flashback blood flow from said wire guide and said reservoir means, responsive to canulation of said needle means, entry of the catheter guide wire into said wire guide and removal of the catheter guide wire from said wire guide, respectively.

2. The closed system canulating device of claim 1 wherein said needle means further comprises a hub carried by said reservoir means and an elongated, hollow needle carried by said hub for insertion into the blood vessel.

3. The closed system canulating device of claim 2 wherein one end of said wire guide projects into said hub and terminates in spaced relationship with respect to said needle to define a critical clearance between the wire guide and said needle for passage of the flashback blood from said needle into said reservoir means.

4. The closed system canulating device of claim 3 wherein said valve means is located in the opposite end of said wire guide.

5. The closed system canulating device of claim 4 wherein said valve means further comprises a substantially self-sealing, resilient membrane for receiving the catheter guide wire and sealing said wire guide from blood flow upon insertion and removal of the catheter guide wire.

6. The closed system canulating device of claim 1 wherein said reservoir means is shaped substantially in the configuration of a heart having characteristic symmetrical lobes and further comprising a reservoir tip provided on said reservoir opposite said lobes for receiving said needle means.

7. The closed system canulating device of claim 6 wherein said needle means further comprises a hub carried by said reservoir tip and an elongated, hollow needle carried by said hub for insertion into the blood vessel.

8. The closed system canulating device of claim 7 wherein one end of said wire guide projects into said hub and terminates in spaced relationship with respect to said needle to define a critical clearance between the wire guide and said needle for passage of the flashback blood from said needle into said reservoir means.

9. The closed system canulating device of claim 8 wherein said valve means is located in the opposite end of said wire guide.

10. The closed system canulating device of claim 9 wherein said valve means further comprises a substantially self-sealing, resilient membrane for receiving the catheter guide wire and sealing said wire guide from blood flow upon insertion and removal of the catheter guide wire.

11. The closed system canulating device of claim 5 wherein said reservoir means is shaped substantially in the configuration of a cylinder and further comprising a reservoir tip provided on one end of said cylinder for receiving said hub.

12. The closed system canulating device of claim 2 wherein one end of said wire guide projects into said hub and further comprising at least one transverse opening provided in said one end, whereby flashback blood flows from said needle through said transverse opening into said reservoir means.

13. The closed system canulating device of claim 12 wherein said valve means is located in the opposite end of said wire guide.

14. The closed system canulating device of claim 13 wherein said valve means further comprises a substantially self-sealing, resilient membrane for receiving the catheter guide wire and sealing said wire guide from blood flow upon insertion and removal of the catheter guide wire.

15. The closed system canulating device of claim 14 wherein said transverse opening further comprises at least one slot.

16. The closed system canulating device of claim 14 wherein said transverse opening further comprises a plurality of spaced holes.

17. A closed system canulating device for preventing uncontrolled flow of blood from a canulated blood vessel during the canulating and guide wire insertion procedures, comprising a needle adapted for canulating a blood vessel and a needle hub receiving said needle in fixed relationship; a reservoir carried by said needle hub for containing flashback blood from said needle when said needle is inserted into the blood vessel; a hollow wire guide extending longitudinally through said reservoir and said needle hub substantially in alignment with said needle, with one end of said wire guide terminating in spaced relationship with respect to said needle to define a critical clearance between said hollow wire guide and said needle; and resilient valve means provided in said hollow wire guide for sealing said hollow wire guide, whereby said flashback blood is directed through said needle and said critical clearance into said reservoir, responsive to canulation of the blood vessel by said needle.

18. The closed system canulating device of claim 17 wherein said valve means further comprises a substantially self-sealing, resilient membrane located in the opposite end of said wire guide, for receiving the catheter guide wire and sealing said wire guide from blood flow upon insertion and removal of the catheter guide wire.

19. A closed system canulating device for preventing uncontrolled flow of blood from a canulated blood vessel during the canulating and guide wire insertion procedures, comprising a needle adapted for canulating a blood vessel and a needle hub receiving said needle in fixed relationship; a reservoir carried by said needle hub for containing flashback blood from said needle when said needle is inserted into the blood vessel; a hollow wire guide extending longitudinally through said reservoir and said needle hub substantially in alignment with said needle, with one end of said wire guide terminating at said needle; at least one transverse opening provided in said one end of said wire guide; and resilient valve means provided in said wire guide for sealing said wire guide, whereby said flashback blood is directed through said needle into said wire guide and through said transverse opening into said reservoir, responsive to canulation of the blood vessel by said needle.

20. The closed system canulating device of claim 19 wherein said valve means further comprises a substantially self-sealing, resilient membrane located in the opposite end of said wire guide, for receiving the catheter guide wire and sealing said wire guide from blood flow upon insertion and removal of the catheter guide wire.

* * * * *